US012672917B2

(12) United States Patent　(10) Patent No.:　US 12,672,917 B2
Assaker et al.　(45) Date of Patent:　Jul. 7, 2026

(54) DEVICE AND METHOD FOR GENERATING A 3D BIOMECHANICAL MODEL OF A SPINE OF A PATIENT AND ASSISTING A USER IN PLANNING A SPINE TREATMENT FOR SAID PATIENT'S SPINE

(71) Applicant: MDSIM, Esch-sur-Alzette (LU)

(72) Inventors: Roger Assaker, Esch-sur-Alzette (LU); Richard Assaker, Esch-sur-Alzette (LU); Laurent Adam, Esch-sur-Alzette (LU); Florent Hannard, Esch-sur-Alzette (LU)

(73) Assignee: MDSIM, Esch-sur-Alzette (LU)

( * ) Notice: Subject to any disclaimer, the term of this patent is extended or adjusted under 35 U.S.C. 154(b) by 0 days.

(21) Appl. No.: 19/213,227

(22) Filed: May 20, 2025

(65) Prior Publication Data

US 2025/0366923 A1　Dec. 4, 2025

(30) Foreign Application Priority Data

May 31, 2024　(EP) ..................................... 24179379

(51) Int. Cl.
*A61B 34/10*　(2016.01)
*G06T 17/00*　(2006.01)
*G16H 20/40*　(2018.01)

(52) U.S. Cl.
CPC .............. *A61B 34/10* (2016.02); *G06T 17/00* (2013.01); *G16H 20/40* (2018.01); *A61B 2034/104* (2016.02); *A61B 2034/105* (2016.02); *G06T 2200/04* (2013.01); *G06T 2210/41* (2013.01)

(58) Field of Classification Search
CPC .............. A61B 34/10; A61B 2034/104; A61B 2034/105; G06T 17/00; G06T 2200/04; G06T 2210/41; G16H 20/40
See application file for complete search history.

(56) References Cited

U.S. PATENT DOCUMENTS

| | | | |
|---|---|---|---|
| 8,126,234 B1 * | 2/2012 | Edwards ................. | G06T 19/20 |
| | | | 382/128 |
| 2004/0009459 A1 * | 1/2004 | Anderson ............... | G06T 19/00 |
| | | | 703/11 |
| 2007/0093998 A1 * | 4/2007 | El-Baroudi ............ | G16H 50/50 |
| | | | 703/11 |
| 2019/0146458 A1 | 5/2019 | Roh et al. | |

OTHER PUBLICATIONS

European Search Report issued by the European Patent Office (EPO) of corresponding EP Application No. EP24179379, Date of completion of the search: Oct. 22, 2024.

* cited by examiner

*Primary Examiner* — Sing-Wai Wu
(74) *Attorney, Agent, or Firm* — Maier & Maier, PLLC

(57)　ABSTRACT

The present invention relates to a device and method for generating a geometrical model and a 3D biomechanical model of a spine of a patient and assisting a user in planning a spine treatment for said patient's spine. The present invention further relates to a surrogate model. The 3D biomechanical model and the surrogate model may be configured to generate biomechanical performance indicators and clinical indicators.

13 Claims, 6 Drawing Sheets

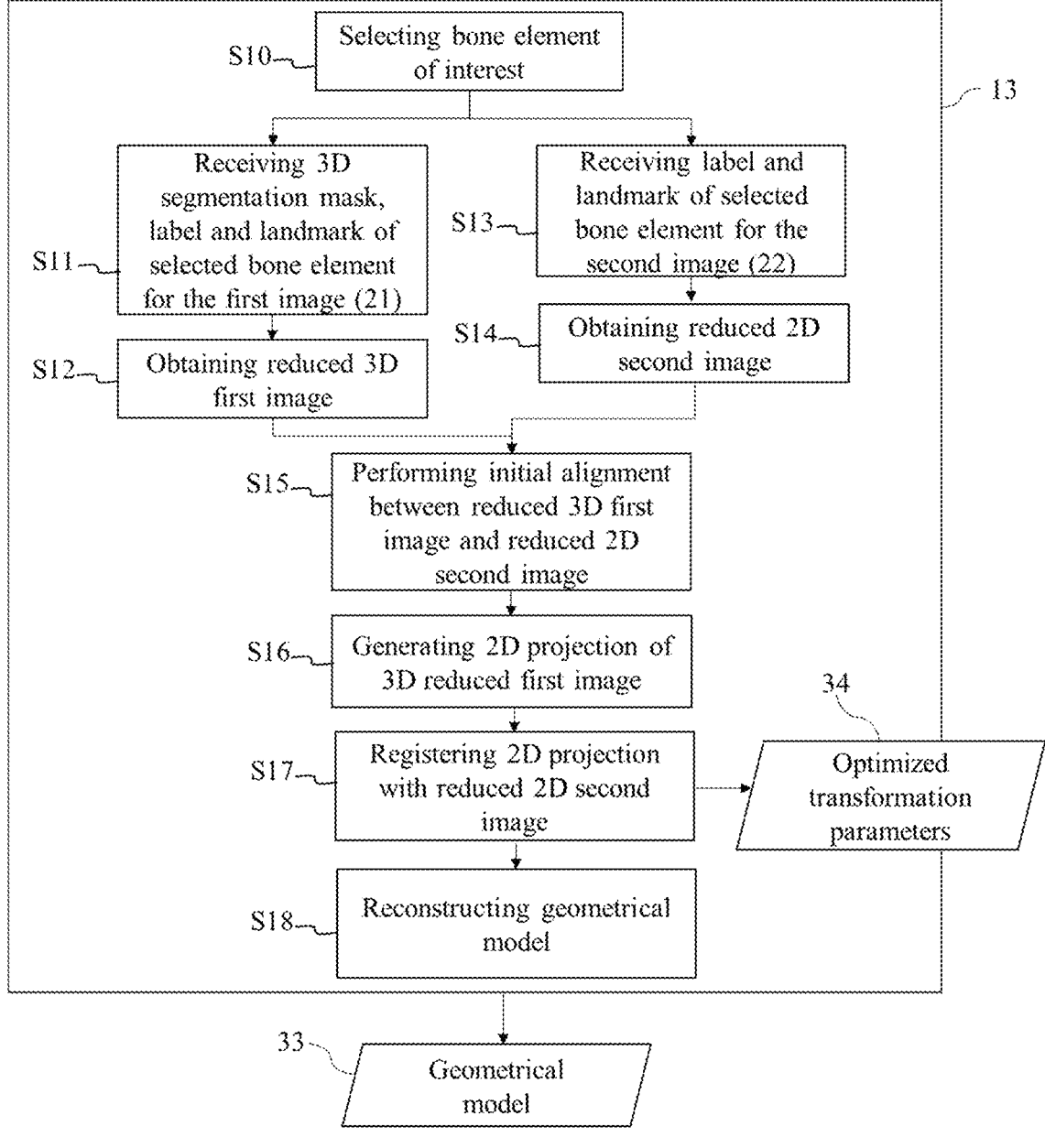

S10 — Selecting bone element of interest

13

S11 — Receiving 3D segmentation mask, label and landmark of selected bone element for the first image (21)

S13 — Receiving label and landmark of selected bone element for the second image (22)

S12 — Obtaining reduced 3D first image

S14 — Obtaining reduced 2D second image

S15 — Performing initial alignment between reduced 3D first image and reduced 2D second image S16 — Generating 2D projection of 3D reduced first image S17 — Registering 2D projection with reduced 2D second image 34 — Optimized transformation parameters S18 — Reconstructing geometrical model 33 — Geometrical model

FIG. 5

DEVICE AND METHOD FOR GENERATING A 3D BIOMECHANICAL MODEL OF A SPINE OF A PATIENT AND ASSISTING A USER IN PLANNING A SPINE TREATMENT FOR SAID PATIENT'S SPINE

RELATED APPLICATIONS

The present application claims the benefit under 35 U.S.C. § 119(a)-(d) to European Patent Application No. EP 24179379, filed on May 31, 2024, entitled "DEVICE AND METHOD FOR GENERATING A 3D BIOMECHANICAL MODEL OF A SPINE OF A PATIENT AND ASSISTING A USER IN PLANNING A SPINE TREATMENT FOR SAID PATIENT'S SPINE", the entire disclosure of which is hereby incorporated by reference in its entirety under 37 C.F.R. § 1.57. Any and all applications for which a foreign or domestic priority claim is identified in the Application Data Sheet as filed with the present application are hereby incorporated by reference under 37 C.F.R. § 1.57.

FIELD OF INVENTION

The present invention relates to the technical field of medical imaging processing for use in spine interventions and spine treatment (e.g. such as planning surgeries, educating surgeons, developing therapies and developing spine medical devices). More precisely, the invention pertains to a device and method for generating a 3D biomechanical model of a spine of a patient and assisting a user in planning a spine treatment for said patient's spine.

BACKGROUND OF INVENTION

Spine degeneration and spine deformities encompass a spectrum of conditions including scoliosis, segmental deformities, trauma, tumors, and osteoporosis. These conditions collectively affect millions of individuals worldwide, spanning various age groups and demographics, and pose significant challenges to their overall well-being and daily functioning. From the debilitating curvature of scoliosis to the progressive deterioration associated with degenerative disc disease, spine deformities impose substantial limitations on mobility, comfort, and quality of life.

Spine interventions and treatment is crucial to alleviate the symptoms and functional impairments caused by spine deformities. The success of such treatment procedures is typically assessed through a comprehensive evaluation that encompasses various parameters. These include not only the subjective experience of the patient, such as improvements in symptoms and pain relief, but also objective measures such as radiographic evidence and visible correction of spinal posture. Achieving favorable outcomes across these diverse metrics is paramount in determining the overall success of spinal surgery and its impact on patient health and well-being.

Despite the promising outcomes observed in the short-term following spinal surgery, a significant proportion of patients fail to experience sustained relief from their symptoms or achieve the desired correction of underlying spinal pathology. For instance, studies indicate that more than 40% of adult spine realignment surgeries encounter complications necessitating revision procedures. Such challenges underscore the inherent complexities involved in addressing spine deformities surgically.

Notably, the high incidence of postoperative complications and suboptimal outcomes underscores the critical importance of enhancing the success rates of spinal surgeries.

SUMMARY

This invention thus relates to a computer implemented method for generating a 3D biomechanical model of a spine of a patient and assisting a user in planning a spine treatment for said patient's spine, said 3D biomechanical model being representative of bone elements associated to said patient's spine, surrounding tissue elements and associated biomechanical parameters said method comprising:

receiving medical data related to said patient, said medical data comprising at least: a weight, a height, clinical information and morphological information;

receiving at least one first image of said patient, said at least one first image being previously acquired from said patient in a first position, and comprising at least one first representation of bone elements in said first position;

receiving at least one second image of said patient, said at least one second image being previously acquired from said patient in a second position different from said first position, and comprising at least one second representation of said bone elements in said second position;

generating a geometrical model of said patient's spine based on said at least one first image and said at least one second image, said geometrical model being representative of said bone elements of said patient's spine;

generating an intermediate geometrical model based on said geometrical model on which a model of the surrounding tissue elements is added;

computing a mass distribution of said patient based on the intermediate geometrical model and at least one of: said medical data received, said at least one first image and said at least one second image;

computing biomechanical parameters based on said at least one among: said clinical information, said at least one first image and/or said at least one second image, said biomechanical parameters being related to biomechanical properties of said bone elements and said surrounding tissue elements;

generating said 3D biomechanical model representative of bone elements associated to said patient's spine, surrounding tissue elements and associated biomechanical parameters based on said intermediate geometrical model, said mass distribution and said biomechanical parameters; and outputting said 3D biomechanical model to assist said user in scheduling said surgery on said patient's spine.

According to the invention, assisting a user in planning a spine treatment for said patient's spine encompasses multiple aspects of spine care, including training surgeons through simulated treatment scenarios based on the patient's unique anatomy, planning surgeries by providing detailed preoperative assessments, planning non-invasive therapies such as kinesiotherapy by providing insights into the biomechanical characteristics of the patient's spine, including simulating therapeutic exercises and evaluating their potential impact on the patient's condition. Furthermore, the invention extends to the creation of custom medical devices specially fitted to the patient's anatomy.

Advantageously the computer implemented method according to the present invention allows to obtain a robust 3D biomechanical model with detailed insights into the patient's spinal anatomy, based on only two images acquired with two different imaging modalities. The 3D biomechanical model of the spine advantageously includes the relative position of the different bone elements (e.g. at least one of a cervical vertebra, a thoracic vertebra, a lumbar vertebra, the sacrum and/or the coccyx) comprised in the patient's spine, the surrounding soft tissues (e.g. intervertebral discs, tendons, ligaments, muscles) and biomechanical parameters.

The 3D biomechanical model from the invention advantageously allows visualization of the specific degenerations, deformities or pathologies of the patient's spine and the spatial relationships between the different anatomical structures (e.g. bone elements and tissue elements). This further allows to plan the potential outcome of spine interventions and spine treatment that are specifically tailored to the patient's unique anatomy.

Thanks to the 3D biomechanical model, surgeons can simulate preoperatively various treatment techniques and evaluate their potential outcomes before performing the actual procedure. This virtual rehearsal helps in identifying potential challenges, optimizing treatment workflows, and reducing treatment time, thereby enhancing treatment efficiency and patient safety. For instance, surgeons can accurately assess the size, shape, and placement of implants required for a spine surgery. This enables them to select the most suitable implants that match the patient's anatomy, leading to better postoperative outcomes and reduced risk of complications such as implant migration or failure.

During surgery, the 3D biomechanical model can help with intraoperative navigation, providing real-time feedback to surgeons during the procedure. This assists surgeons in navigating the complex anatomical structures of the spine accurately, reducing the risk of intraoperative complications and improving treatment precision.

After surgery, the 3D biomechanical model can serve as a reference for postoperative assessment and follow-up.

According to the invention, the biomechanical parameters may include spinal curvature, bone elements motion (e.g. the degree of movement and range of motion of each individual bone element compared to the other bone elements), bone density, bone porosity, bone strength (e.g. the ability of bone tissue to withstand applied loads without fracturing), bone stiffness, intervertebral disc properties, ligament properties, muscle quality. Additionally, when the patient is already equipped with a medical device (e.g. such as implants, rods, hooks, screws, plates, artificial disks), the biomechanical parameters may include parameters of said medical device such as the position of the medical device, the quality of the adhesion between at least one part of the medical device and the bony structure of the patient's spine, stiffness and/or strength of the medical device.

According to other advantageous aspects of the invention, the device comprises one or more of the features described in the following embodiments, taken alone or in any possible combination.

According to one embodiment, said method further comprises computing geometrical measurements on said geometrical model, said geometrical measurements being related to geometrical parameters computed between at least two bone elements of the geometrical model.

According to one embodiment, said method further comprises:

applying at least one load to said 3D biomechanical model, said load including at least one a flexion load and an extension load, computing biomechanical performance indicators related to biomechanical stress between at least two bone elements based on the 3D biomechanical model obtained after said load has been applied, computing clinical indicators based on said biomechanical performance indicators.

According to one embodiment, said at least one first image comprises at least one 3D image and said at least one second image comprises at least one 2D image.

According to one embodiment, said at least one 2D image may be at least one of: an X-ray image acquired by an X-ray imaging system, such as for example EOS imaging, or an Orthopedic imaging System.

According to one embodiment, said at least one 3D image may be a least one of: a Computed Tomography (CT) scan and/or an image acquired by a Magnetic Resonance Imaging (MRI) system.

According to one embodiment, generating said geometrical model of said patient's spine comprises:

selecting at least one bone element of interest among the bone elements associated to said patient's spine;

receiving at least one 3D segmentation mask of at least one bone element represented in the first 3D image including the bone element of interest, at least one associated label and at least one landmark calculated for said at least one bone element represented in said at least one first 3D image, and receiving at least one label associated to at least one bone element represented in said at least one second 2D image and at least one landmark calculated for said at least one bone element represented in said at least one second 2D image;

for each bone element of interest:

obtaining from said first segmentation mask at least one 3D reduced first image comprising said bone element of interest and a surrounding region of said bone element of interest;

obtaining at least one 2D reduced second image comprising said bone element of interest and a surrounding region of said bone element of interest;

performing an initial alignment between said at least one 3D reduced first image and at least one 2D reduced second image;

generating at least one 2D projection of said at least one 3D reduced first image;

registering said at least one 2D projection to said at least one 2D reduced second image with respect to said bone element of interest so as to obtain optimized transformation parameters corresponding to said bone element of interest;

reconstructing said geometrical model using the at least one 3D segmentation mask and the optimized transformation parameters obtained for each corresponding bone element of interest, so that the geometrical model provides a representation of at least one portion of the patient's spine in the second position.

According to one embodiment, in the first position the patient is lying down and the second position the patient is standing.

The invention addresses the challenge of constructing a model based on two images obtained through different imaging modalities, where the patient assumes distinct positions. Indeed, each position imposes different forces on the spine and surrounding soft tissues, directly influencing their mechanical behavior. For instance, the difficulty associated with constructing a 3D model based on images where the patient is standing and images where the patient is lying down primarily stems from the differences in the patient's body positioning and spinal alignment between the two scenarios. When standing, the spine experiences gravitational forces differently compared to when lying down, resulting in variations in spinal curvature, vertebral alignment, and tissue deformation. Additionally, the distribution of body weight and muscle tension differs between standing and lying positions, further influencing the shape and configuration of the spine. The 3D biomechanical model is advantageously obtained through the precise alignment of each individual bone element from the first image (e.g. 3D image) with its counterparts in the second image (e.g. 2D image).

According to one embodiment, said at least one landmark for the at least one first 3D image and second 2D image is chosen from the following: a center, and/or corner points of said at least one bone element.

According to one embodiment, said optimized transformation parameters comprise at least one of: a rotation parameter and/or a translation parameter.

According to one embodiment, reconstructing said geometrical model comprises:

for each bone element of interest, applying the corresponding optimized transformation parameters to the bone element of interest in the at least one 3D segmentation mask, obtaining an individual segmentation mask corresponding to said bone element of interest in the second position, verifying and removing interpenetrations in between individual segmentation masks.

According to one embodiment, said 3D biomechanical model is a finite-element model.

According to the invention, a finite-element model refers to a computational representation of a physical system or structure, such as the human spine, using the finite element method (FEM). The finite element method is a numerical technique used to solve complex problems by dividing a continuous system into smaller, discrete elements. In the case of biomechanical modeling of the spine, a finite-element model involves discretizing the spine into smaller elements (e.g. bone elements). Each element represents a portion of the spine, and the behavior of these elements is governed by mathematical equations that describe how they respond to applied forces, loads, and boundary conditions. By solving these equations iteratively, the finite element method allows users to simulate the mechanical behavior of the spine under different conditions.

According to one embodiment, the method according to the invention further comprises computing, using a surrogate model, at least one post-treatment biomechanical performance indicator comprising information concerning said patient's spine after performing at least one treatment act, said surrogate model being a machine learning model, previously trained on a training dataset, said surrogate model being configured to receive as input said geometrical model, said geometrical measurements, said biomechanical parameters, said biomechanical performance indicators, said clinical indicators, and said at least one treatment act to be performed, wherein said training dataset comprises a plurality of training sample obtained from a plurality of subjects, each training sample comprising a 3D biomechanical model of a spine of a subject and the corresponding medical data, geometrical model, geometrical measurements, biomechanical parameters, biomechanical performance indicators, clinical indicators, and treatment acts.

According to one embodiment, the method according to the invention further comprises computing at least one treatment plan by using a set of rules applied to said geometrical parameters and to said biomechanical performance indicators, said clinical indicators and said at least one post-treatment biomechanical performance indicator, said at least one treatment plan comprising at least one treatment act to perform on said patient's spine.

According to one embodiment, said at least one post-treatment biomechanical performance indicator is associated to information comprising computing probabilistic medical indicators representing a probability of mechanical failure of at least one of an implanted device, vertebral bones and intervertebral disks.

According to one embodiment, computing at least one treatment plan comprises comparing said at least one post-treatment biomechanical performance indicator, and the associated information, across different treatment plans to classify the treatment plans as function of a probability of mechanical failure.

According to one embodiment, said plurality of bone element comprises at least one vertebra among S1 to C1 and/or at least one intervertebral disc, and/or at least one surrounding element, said surrounding element comprising at least one of: a hip, a femur head, a rib, ligaments and muscles.

The present invention further relates to a device for generating a 3D biomechanical model of a spine of a patient and assisting a user in planning a spine treatment for said patient's spine, said 3D biomechanical model being representative of bone elements associated to said patient's spine, surrounding tissue elements and biomechanical parameters associated said device comprising:

at least one input configured to:

receive medical data related to said patient, said medical data comprising at least: a weight, a height, clinical information and morphological information;

receive at least one first image of said patient, said at least one first image being previously acquired from said patient in a first position, and comprising at least one first representation of bone elements in said first position;

receive at least one second image of said patient, said at least one second image being previously acquired from said patient in a second position different from said first position, and comprising at least one second representation of said bone elements in said second position;

at least one processor configured to:

generate a geometrical model of said patient's spine based on said at least one first image and said at least one second image, said geometrical model being representative of said bone elements of said patient's spine;

generating an intermediate geometrical model based on said geometrical model on which a model of the surrounding tissue elements is added;

compute a mass distribution of said patient based on the intermediate geometrical model and at least one of: said medical data received, said at least one first image and said at least one second image;

compute biomechanical parameters based on said at least one among: said clinical information, said at least one first image and/or said at least one second image, said biomechanical parameters being related to biomechanical properties of said bone elements and said surrounding tissue elements;

generate said 3D biomechanical model representative of bone elements associated to said patient's spine, surrounding tissue elements and associated biomechanical parameters based on said intermediate geometrical model, said mass distribution and said biomechanical parameters;

at least one output configured to output said geometrical model and said 3D biomechanical model to assist said user in scheduling said surgery on said patient's spine.

In addition, the disclosure relates to a computer program comprising instructions which, when the program is executed by a computer, cause the computer to carry out the computer-implemented method for generating a 3D biomechanical model of a spine of a patient and assisting a user in planning a spine treatment for said patient's spine, compliant with any of the above execution modes.

The present disclosure further pertains to a computer-readable medium comprising instructions which, when executed by a computer, cause the computer to carry out the computer-implemented method for generating a 3D biomechanical model of a spine of a patient and assisting a user in planning a spine treatment for said patient's spine, compliant with any of the above execution modes.

The present disclosure further pertains to a non-transitory program storage device, readable by a computer, tangibly embodying a program of instructions executable by the computer to perform the computer-implemented method for generating a 3D biomechanical model of a spine of a patient and assisting a user in planning a spine treatment for said patient's spine, compliant with the present disclosure.

Such a non-transitory program storage device can be, without limitation, an electronic, magnetic, optical, electromagnetic, infrared, or semiconductor device, or any suitable combination of the foregoing. It is to be appreciated that the following, while providing more specific examples, is merely an illustrative and not exhaustive listing as readily appreciated by one of ordinary skill in the art: a portable computer diskette, a hard disk, a ROM, an EPROM (Erasable Programmable ROM) or a Flash memory, a portable CD-ROM (Compact-Disc ROM).

DEFINITIONS

In the present invention, the following terms have the following meanings:

The terms "adapted" and "configured" are used in the present disclosure as broadly encompassing initial configuration, later adaptation or complementation of the present device, or any combination thereof alike, whether effected through material or software means (including firmware).

The term "processor" should not be construed to be restricted to hardware capable of executing software, and refers in a general way to a processing device, which can for example include a computer, a microprocessor, an integrated circuit, or a programmable logic device (PLD). The processor may also encompass one or more Graphics Processing Units (GPU), whether exploited for computer graphics and image processing or other functions. Additionally, the instructions and/or data enabling to perform associated and/or resulting functionalities may be stored on any processor-readable medium such as, e.g., an integrated circuit, a hard disk, a CD (Compact Disc), an optical disc such as a DVD (Digital Versatile Disc), a RAM (Random-Access Memory) or a ROM (Read-Only Memory). Instructions may be notably stored in hardware, software, firmware or in any combination thereof.

"Machine learning (ML)" designates in a traditional way computer algorithms improving automatically through experience, on the ground of training data enabling to adjust parameters of computer models through gap reductions between expected outputs extracted from the training data and evaluated outputs computed by the computer models.

"Datasets" are collections of data used to build an ML mathematical model, so as to make data-driven predictions or decisions. In "supervised learning" (i.e. inferring functions from known input-output examples in the form of labelled training data), three types of ML datasets (also designated as ML sets) are typically dedicated to three respective kinds of tasks: "training", i.e. fitting the parameters, "validation", i.e. tuning ML hyperparameters (which are parameters used to control the learning process), and "testing", i.e. checking independently of a training dataset exploited for building a mathematical model that the latter model provides satisfying results.

A "neural network (NN)" designates a category of ML comprising nodes (called "neurons"), and connections between neurons modeled by "weights". For each neuron, an output is given in function of an input or a set of inputs by an "activation function". Neurons are generally organized into multiple "layers", so that neurons of one layer connect only to neurons of the immediately preceding and immediately following layers.

"(Data points) registration" refers to the process of transforming different sets of data points into one coordinate system. Image registration involves spatially transforming "moving" data points to align with "target" data points (i.e., image, model and the like). The reference frame (i.e.; referential) associated to the target data points is stationary, while the other datasets are transformed to match to the target.

BRIEF DESCRIPTION OF THE DRAWINGS

The present disclosure will be better understood, and other specific features and advantages will emerge upon reading the following description of particular and non-restrictive illustrative embodiments, the description making reference to the annexed drawings wherein:

FIG. 5 is a flow chart showing successive steps executed to generate the geometrical model from FIG. 1;

ILLUSTRATIVE EMBODIMENTS

The present description illustrates the principles of the present disclosure. It will thus be appreciated that those skilled in the art will be able to devise various arrangements that, although not explicitly described or shown herein, embody the principles of the disclosure and are included within its scope.

All examples and conditional language recited herein are intended for educational purposes to aid the reader in understanding the principles of the disclosure and the concepts contributed by the inventor to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Thus, for example, it will be appreciated by those skilled in the art that the block diagrams presented herein may represent conceptual views of illustrative circuitry embodying the principles of the disclosure. Similarly, it will be appreciated that any flow charts, flow diagrams, and the like represent various processes which may be substantially represented in computer readable media and so executed by a computer or processor, whether or not such computer or processor is explicitly shown.

The functions of the various elements shown in the figures may be provided through the use of dedicated hardware as well as hardware capable of executing software in association with appropriate software. When provided by a processor, the functions may be provided by a single dedicated processor, a single shared processor, or a plurality of individual processors, some of which may be shared.

It should be understood that the elements shown in the figures may be implemented in various forms of hardware, software or combinations thereof. Preferably, these elements are implemented in a combination of hardware and software on one or more appropriately programmed general-purpose devices, which may include a processor, memory and input/output interfaces.

Figure 1:
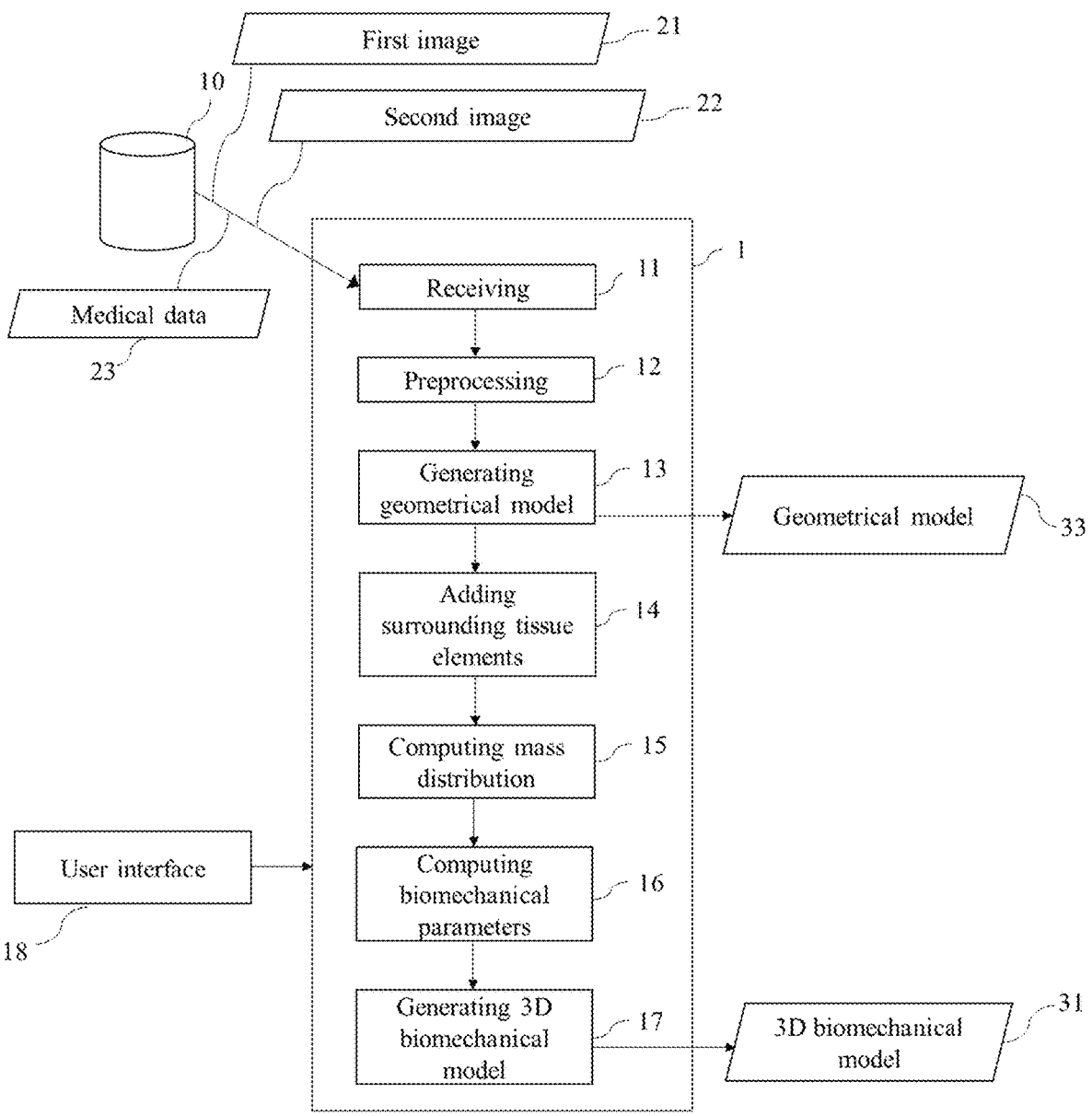
FIG. 1 is a block diagram representing schematically a particular mode of a device for generating a 3D biomechanical model of a spine of a patient and assisting a user in planning a spine treatment for said patient's spine compliant with the present disclosure.

The present disclosure will be described in reference to a particular functional embodiment of a device 1 for generating a 3D biomechanical model of a spine of a patient and assisting a user in planning a spine treatment for said patient's spine, as illustrated on FIG. 1.

The device 1 is adapted to receive as input at least one first image 21 of the patient and at least one second image 22 of said patient and medical data 23 pertaining to the patient.

The device 1 is adapted to output a 3D biomechanical model 31 of the spine of a patient and a geometrical model 33 of the patient's spine.

The device 1 is configured to generate the geometrical model 33 as illustrated on FIG. 5, based notably on the at least one first image 21 of the patient and the at least one second image 22 of said patient received as input by said device 1.

Though the presently described device 1 is versatile and provided with several functions that can be carried out alternatively or in any cumulative way, other implementations within the scope of the present disclosure include devices having only parts of the present functionalities.

The device 1 is advantageously an apparatus, or a physical part of an apparatus, designed, configured and/or adapted for performing the mentioned functions and produce the mentioned effects or results. In alternative implementations, the device 1 is embodied as a set of apparatus or physical parts of apparatus, whether grouped in a same machine or in different, possibly remote, machines. The device 1 may e.g. have functions distributed over a cloud infrastructure and be available to users as a cloud-based service, or have remote functions accessible through an API.

In what follows, the modules are to be understood as functional entities rather than material, physically distinct, components. They can consequently be embodied either as grouped together in a same tangible and concrete component, or distributed into several such components. Also, each of these modules are possibly themselves shared between at least two physical components. In addition, the modules are implemented in hardware, software, firmware, or any mixed form thereof as well. They are preferably embodied within at least one processor of the device 1.

The device 1 comprises a module 11 for receiving the following input data: at least one first image 21, at least one second image 22 and medical data 23 pertaining to the patient. All these input data may be stored in one or more local or remote database(s) 10. The latter can take the form of storage resources available from any kind of appropriate storage means, which can be notably a RAM or an EEPROM (Electrically-Erasable Programmable Read-Only Memory) such as a Flash memory, possibly within an SSD (Solid-State Disk).

More precisely, the at least one first image 21 may comprise one image or several images acquired on a same patient using a same imaging modality or different imaging modalities. For instance, the at least one first image 21 may be a 3D image. The at least one first image 21 may comprise at least one image acquired using a Computer Tomography (CT)-scanner and/or at least one image acquired using a Magnetic Resonance Imaging (MRI) system.

During acquisition of the first images 21, the patient is in a first position. For instance, in the case of images acquired using CT-scanners or MRI systems, the patient is often lying down on a flat scanning table. The patient may either be positioned o its back or on its stomach on the scanning table.

The at least one second image 22 may comprise one image or several images acquired on the same patient, using at least one imaging modality, different from the imaging modality used to acquire the first images 21. For instance, the at least one second image 22 may be a 2D image. The at least one second image 22 may comprise at least one image acquired using an X-ray imaging system and/or an EOS (Electrical Optical Synergy) imaging system and/or an Orthopedic Imaging System.

During acquisition of the second images 22, the patient is in a second position. The second position may be a weight-bearing position in which the body is supporting its own weight against gravity. For instance, in the case of images acquired using X-ray imaging systems, EOS imaging system or Orthopedic Imaging System, the patient may be in a standing or sitting position.

In the specific case of EOS imaging, the patient is typically positioned standing or sitting between two vertical imaging plates, wherein one vertical imaging plate is positioned perpendicular to the other vertical imaging plate. These plates capture multiple X-ray images as they move synchronously along the patient's body, allowing for the acquisition of full-body or region-specific images.

The medical data 23 received by the device 1 are metadata and may comprise clinical information and morphological information collected during previous examinations. The medical data 23 may comprise a list of symptoms (nature, number, duration, severity), physical examination findings (functional status, neurological assessments such as motor strength, sensory deficit or reflexes), laboratory test results, medical and treatment history of the patient (previous spinal surgeries, spinal disorders, relevant comorbidities, current and past medications, including pain management and anti-coagulation therapy), together with anthropometric measurements (height, weight, body mass index (BMI)).

The device 1 may further comprise a module 12 configured to preprocess the at least one first image 21, at least one second image 22 and the medical data 23 Preprocessing may include image resizing, cropping, segmentation, labelling, landmarking, denoising, normalization, augmentation and/or filtering.

The device may further comprise a module 13 for generating a geometrical model 33 of the patient's spine based on the at least one first image 21 and the at least one second image 22.

Notably, as illustrated on FIG. 5, the geometrical model 33 may be generated by dividing the spine of the patient into bone elements and individually aligning each bone element in the first images 21, with its counterpart in the second images 22.

According to the invention, a bone element may comprise at least part of a cervical vertebra, a thoracic vertebra, a lumbar vertebra, the sacrum and/or the coccyx. The bone element may comprise one or several bones among the vertebrae, the sacrum and the coccyx. Additionally, it may at least one of: a hip and/or a femur head and/or a rib.

Generation of the geometrical model 33 may involve selecting S10 at least one bone element of interest among the bone elements previously defined.

For the at least one bone element of interest, the device 1 is configured to receive S11 (for instance via module 11) at least one segmentation mask of bone elements of the patient's spine. In practice, the segmentation mask comprises at least a segmentation of the bone element of interest as represented in the first image 21 and may additionally comprise the immediately surrounding bone elements as represented in the first image 21. In the case where the first image 21 is a 3D image, the segmentation mask is a 3D segmentation mask.

The device 1 may be further configured to receive S11 (for instance via module 11) at least one label associated with the at least one segmentation mask of the bone element of interest.

A label typically refers to a numerical or categorical identifier assigned to the bone element of interest in the segmentation mask. The label serves as an identifier that distinguishes the bone element of interest from other anatomical structures, objects, or regions of interest in the segmentation mask. For instance, the label may correspond to the vertebral segmentation labeling system, that allows identification of the specific position of the bone element within the spine using a letter: C for Cervical vertebrae, T for Thoracic vertebrae, L for Lumbar vertebrae, S for Sacral vertebrae, and a number following the letter, that indicates the specific vertebral level within each region of the spine (e.g. for example C1 for first cervical vertebra, C2 for second cervical vertebra . . . ).

The device 1 may be further configured to receive S11 (for instance via module 11), at least one landmark calculated on the bone element of interest, in the first image 21.

A landmark corresponds to a specific point or features that is identified and quantified to characterize the morphology, orientation, or alignment of the bone element of interest. It might be the center of the bone element of interest and/or the corners of the bone element of interest, such as the Spinous Process Tip of the bone element of interest (e.g. the most prominent and distal point of the spinous process, located at the posterior aspect of the bone element), the Superior Articular Process Tip of the bone element of interest (e.g. the most superior point of the superior articular process, which articulates with the adjacent bone element located above the bone element of interest), the Inferior Articular Process Tip of the bone element of interest (e.g. the most inferior point of the inferior articular process, which articulates with the adjacent bone element located below the bone element of interest), the Transverse Process Tip (e.g. the distal end of the transverse process, extending laterally from the bone element of interest), or specific landmarks on the pedicles such as the Pedicle Entry Point (e.g., the point where the nerve root enters the pedicle). Additionally, landmarks on the anterior and posterior vertebral heights (e.g., the highest points on the anterior and posterior aspects of the bone element of interest) can be used. Furthermore, landmarks at the junctions of the facet joints may also be used. Additionally, attachments points of the bone element with at least one of a ligament and a muscle may also be used. Other points, such as positions of medical devices already implanted in the patient (if applicable) may be used and/or points where a medical device or a treatment act (e.g. such as a cut to a bone element).

The landmarks may for instance be derived from an Atlas such as THUMS or Viva plus.

The device 1 may be further configured to receive S13 (for instance via module 11) at least one label associated with the bone element of interest in the second image 22.

The device 1 may be further configured to receive S13 (for instance via module 11) at least one landmark associated with the bone element of interest in the second image 22.

The segmentation masks, landmarks and labels may be previously stored in one or more local or remote database(s) 10. Alternatively, the device 1 may be configured to generate said segmentation masks using segmentation algorithms such as Thresholding-Based Segmentation algorithms, Region-Based Segmentation algorithms, Edge-Based Segmentation algorithms, Active Contour Models (Snakes), or Atlas-Based Segmentation algorithms. Moreover, the device 1 may be configured to annotate the landmarks on the bone elements of interest in either the segmentation masks and/or the second images 22 and/or to associate the label with the bone element of interest in either the segmentation masks and/or the second images 22.

For instance, landmark annotation may be performed using an annotation model comprising a Residual Network with 34 layers and skip connections pre-trained using an image dataset constructed using images from the ImageNet database, followed by a bottleneck and a decoder with skip connections. The training may occur in two stages: first with a weighted root mean square error loss function and then with a weighted dice loss function. An Adam optimizer with a constant learning rate of $10^{-4}$ may be used. The annotation model may output heatmaps for each landmark.

The device 1 may further be configured to obtain S12 from the at least one segmentation mask at least one reduced first image comprising said bone element of interest and a surrounding region of said bone element of interest. In the case where the first image is a 3D image, the at least one reduced first image is a reduced 3D first image.

The device 1 may further be configured to obtain S14 at least one reduced second image comprising said bone element of interest and a surrounding region of said bone element of interest. In the case where the second image is a 2D image, the at least one reduced second image is a reduced 2D second image.

Such reduced first image and reduced second image may be obtained using region of interest (ROI) cropping or extraction. This process selectively extracts and retains the portion of the image containing the bone element of interest while preserving the spatial dimensions and orientation of the bone element of interest.

The device 1 may further be configured to perform S15 an initial alignment between said at least one reduced first image and at least one reduced second image. The at least one reduced first image and at least one reduced second image are roughly aligned to provide a starting point for the registration process that will follow. This initial alignment can involve simple transformations such as translations, rotations, and scaling to bring the images into approximate alignment. The landmarks present in the at least one reduced first image and at least one reduced second image may be used as reference to perform the rough alignment.

In the case where the reduced first image is a 3D reduced first image, the device 1 may further be configured to generate S16 at least one 2D projection of the at least one 3D reduced first image. Such projection may for instance be obtained using at least one of an orthographic projection or a volumetric projection. For instance, Digitally Reconstructed Radiography (DRR) may be used to obtain the at least one 2D projection based on the 3D reduced first image. DRR involves generating a simulated 2D X-ray image, often in the form of a 2D radiographic projection, from a 3D volumetric dataset.

The device 1 may further be configured to register S17 the at least one 2D projection with the reduced second image. The aim of such registration is to align the bone element of interest from the at least one 2D projection with the bone element of interest from the at least one reduced second image. Registration may be performed using Landmark-Based Registration or image-based registration. To that end, the at least one 2D projection may be roughly aligned with the reduced second image using simple transformations such as translations, rotations, and scaling, such as rigid scaling. Once the images are roughly aligned, the corresponding landmarks are identified and the initial alignment is refined to minimize the differences between the corresponding landmarks in the two images. This optimization process adjusts the transformation parameters (e.g., translation, rotation, scaling) to maximize the spatial overlap or proximity of the landmarks. The registration algorithm typically minimizes a cost function that quantifies the discrepancy between the positions of corresponding landmarks in the two images. This cost function may be based on metrics such as Euclidean distances, least squares error, or other similarity measures. For instance, the cost function may combine the pixel intensities of the 2D projection with the reduced second image. The cost function may further incorporate a filtering process to enhance certain features or characteristics of the images before comparison. The optimization process iteratively adjusts the transformation parameters until the alignment converges to an optimal solution (e.g. optimized transformation parameters 34). Each iteration updates the transformation based on the calculated alignment error, gradually improving the alignment accuracy.

After obtaining, for each bone element of interest, the optimized transformation parameters 34 between each 2D projection and reduced second image, the optimized transformation parameters 34 are applied to the segmentation masks so as to obtain individual segmentation masks wherein the bone elements are oriented as if the patient was in the second position (when the initial segmentation masks were obtained from the patient in the first position). Interpenetrations between the individual segmentation masks may then be removed.

The geometrical model 33 is obtained by converting the individual segmentation masks, wherein interpenetrations are removed, into meshes using mesh generation software or libraries.

The geometrical model 33 is a representation of the patient's spine is the second position. In practice, the geometrical model 33 is a representation of the patient's spine in a weight-bearing position, such as the standing position.

The device may further comprise a module 14 for generating an intermediate geometrical model comprising both the bone elements associated with said patient's spine and the surrounding tissue elements (e.g. ligaments, and/or muscles and/or intervertebral discs and/or cartilages). Such intermediate geometrical model may be obtained by combining the geometrical model 33 and a model of the surrounding tissue elements. The model of the surrounding tissue elements may be obtained using images such as the first images 21 and/the second images 22 wherein the surrounding elements are visible (e.g. MRI, CT-scan etc.) For instance, the images may be used to deform a statistical shape model (SSM) to the specific morphology of the patient. Alternatively, the model of the surrounding tissue elements may be an atlas selected based on the on the medical data 23 related to said patient (e.g. age, weight, sex etc.).

The device 1 may further comprise a module 15 for computing a spatial distribution of mass on the intermediate geometrical model. Overall, computing the mass distribution is equivalent to assigning a mass to each element of the intermediate geometrical model. The mass assignment may be determined based on the nature of the element (e.g. if it is a bone, a muscle, a cartilage, a ligament, an intervertebral disc etc.). The mass assignment may further take into account the medical data 23 received by module 11 (the medical data mainly come from the spine or from the soft tissue surrounding the spine). For instance, if the patient has osteoporosis or is aged, the mass assigned to bone elements will be decreased compared to a normal person.

Additionally, the mass distribution may be computed based on a Body Mass Index (BMI) morphing from an Atlas and/or from a picture of the patient.

The device 1 may further comprise a module 16 for computing biomechanical parameters based on the medical data 23, the at least one first image 21 and/or the at least one second image 22 received by module 11 (for instance, the gray scale of the first image 21 and second image 22 can be used to compute the corresponding biomechanical parameters). The biomechanical parameters transcribe biomechanical properties of the bone elements and the surrounding tissue elements from the patient's spine. They may include material properties such as bone density, bone porosity, bone elasticity, and stiffness derived from the medical data 23 received as input, together with spinal curvature, bone elements motion (e.g. the degree of movement and range of motion of each individual bone element compared to the other bone elements), bone strength (e.g. the ability of bone tissue to withstand applied loads without fracturing), intervertebral disc properties, ligament properties, muscle forces.

The device 1 may further comprise a module 17 for generating the 3D biomechanical model 31 based on the intermediate geometrical model, augmented with the calculated mass distribution and biomechanical parameters.

The 3D biomechanical model 31 may for instance be a finite element model (FEM). To that end, the mass distribution and biomechanical parameters may be used as boundary conditions of the FEM 3D biomechanical model 31. FEM analysis employing numerical solvers may be conducted to solve the equations of motion and deformation for the FEM 3D biomechanical model 31 under the defined boundary conditions.

The 3D biomechanical model 31 may model (in addition with the patient's spine anatomy) at least one medical device (e.g. implant, screw etc.) comprised in the vicinity of the patient's spine.

Once the 3D biomechanical model 31 generated, the module 17 is configured to output the 3D biomechanical model 31 and the geometrical model 33. They may be stored in one or more local or remote database(s) 10, which can take the form of storage resources available from any kind of appropriate storage means, which can be notably a RAM or an EEPROM (Electrically-Erasable Programmable Read-Only Memory) such as a Flash memory, possibly within an SSD (Solid-State Disk).

Figure 3:
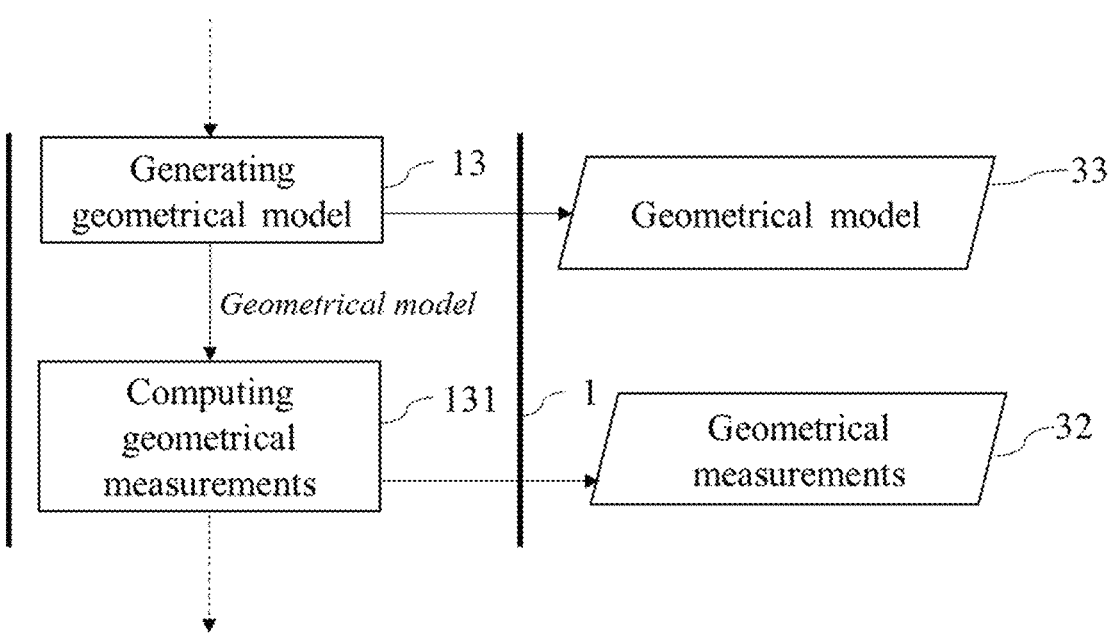
FIG. 3 is a block diagram representing schematically a second mode of the device for generating a 3D biomechanical model of a spine of a patient and assisting a user in planning a spine treatment for said patient's spine compliant with the present disclosure according to FIG. 1.

The device 1 may further comprise a module 131 (see FIG. 3) for computing geometrical measurements 32 on said geometrical model 33. Such geometrical measurements 32 may for instance be distance measurements between specific points or landmarks of the bone elements comprised in the geometrical model 33, such as for instance the distance between the centers of two consecutive bone elements. The geometrical measurements 32 may also be angulation, area, volume measurements and/or curvature analysis.

Figure 4:
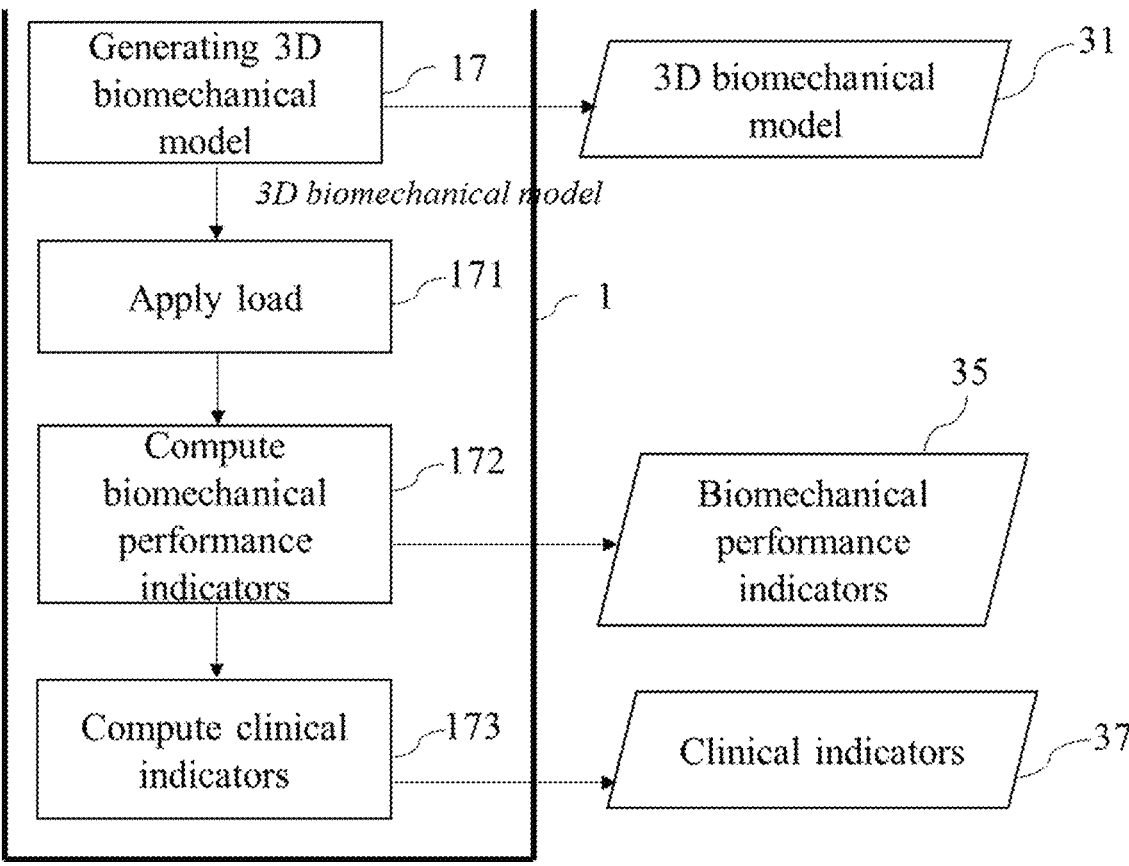
FIG. 4 is a block diagram representing schematically a third mode of the device for generating a 3D biomechanical model of a spine of a patient and assisting a user in planning a spine treatment for said patient's spine compliant with the present disclosure according to FIG. 1.

Further to the generation of the 3D biomechanical model 31, the device 1 may comprise a module 171 (see FIG. 4) for applying load to the 3D biomechanical model 31 an observe how the 3D biomechanical model 31 reacts to the application of such loads by computing (using module 172) biomechanical performance indicators 35, 135.

The loads applied may for instance be extension load, flexion loads or compression loads. The loads may be point loads (e.g. concentrated forces applied at specific points of the 3D biomechanical model 31 that may simulate localized forces such as muscle insertions or external impacts) and/or surface loads (e.g. distributed forces or pressures over surfaces that may simulate contact pressures or muscle forces over an area) and/or body forces (e.g. simulate a movement of the body such as a flexion to catch an object). An appropriate solver may then be chosen and the simulation may be run to solve for displacements, stresses, and strains within the 3D biomechanical model 31.

The biomechanical performance indicators 35, 135 may encompass the calculations performed on the 3D biomechanical model 31 after simulation of loads application. The calculations may include biomechanical stresses between at least two bone elements and/or the calculation of failure risks of a medical device implanted in the patient. Examples of such biomechanical performance indicators 35, 135 may also include determining the maximum Von Mises stress, which is the highest stress experienced by the bones and offers insight into potential failure points. Additionally, the analysis may involve assessing peak strain, indicating the extent of deformation under applied loads and providing information about bone elasticity. Furthermore, evaluation of stress distribution patterns within the bone elements offers valuable data on regions of concentrated stress, aiding in identifying areas susceptible to injury or degeneration. These indicators collectively contribute to a comprehensive understanding of the mechanical behavior of the spine, facilitating informed clinical decision-making and enhancing treatment planning processes.

Furthermore, clinical indicators 37, 137 can be derived from the biomechanical performance indicators 35, 135 to enhance diagnostic and treatment strategies. For instance, one may compute vertebral alignment parameters, such as Pelvic Incidence, Lombar Lordosis, GAP score, Cobb angle measurements, which are crucial for assessing spinal alignment and monitoring conditions like spine deformities or spine degeneration, such as scoliosis. Additionally, biomechanical models enable the calculation of the stresses linked to an implanted medical device and predict the risk of mechanical failure. Moreover, biomechanical models enable the calculation of intervertebral disc stresses, aiding in the evaluation of disc degeneration and guiding interventions for conditions such as disc herniation. Moreover, the analysis may involve estimating segmental range of motion, providing insights into spinal flexibility and facilitating treatment planning for procedures like spinal fusion. These clinical indicators derived from the 3D biomechanical model contribute to a comprehensive understanding of spinal pathologies, enhancing patient care and treatment outcomes.

To determine the clinical indicators 37, 137 a machine learning predictive model may be trained to generate the clinical indicators 37, 137 using a training dataset comprising biomechanical performance indicators 35, 135 paired with clinical indicators 37, 137.

After a spine treatment, the process described above may be performed anew using new images captured on the patient after receiving the treatment. Post-treatment biomechanical performance indicators 235 and post-treatment clinical indicators 131 may then be determined and compared to the biomechanical performance indicators 35, 135 and clinical indicators 37, 137 calculated before spine treatment. This allows to derive conclusions on the efficiency of the spine treatment and help the physician in deciding the next steps of therapy.

Figure 2:
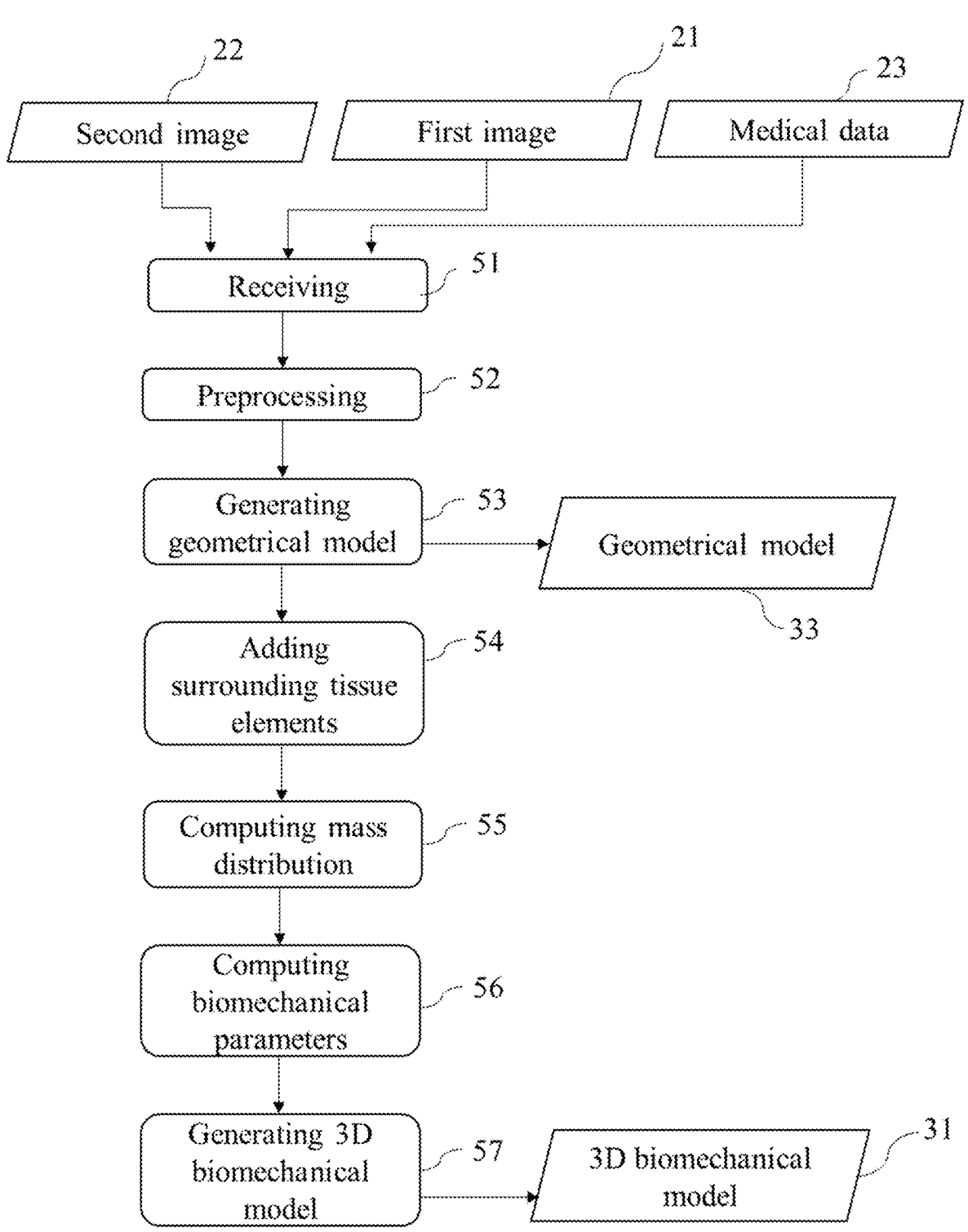
FIG. 2 is a is a flow chart showing successive steps executed with the device of FIG. 1.

In its automatic actions, the device 1 may for example execute the following process (FIG. 2):

receiving medical data 23 related to said patient, at least one first image 21 of said patient, said at least one first image being previously acquired from said patient in a first position, and comprising at least one first representation of bone elements in said first position, and at least one second image 22 of said patient, said at least one second image being previously acquired from said patient in a second position different from said first position, and comprising at least one second representation of said bone elements in said second position (step 51);

optionally preprocessing said medical data 23, said at least one first image 21 and said at least one second image 22 (step 52);

generating the geometrical model 33 of said patient's spine based on said at least one first image 21 and said at least one second image 22 (step 53);

optionally computing geometrical measurements 32 on said geometrical model 33, said geometrical measurements being related to geometrical parameters computed between at least two bone elements of the geometrical model 33;

generating an intermediate geometrical model based on the geometrical model 33 on which a model of the surrounding tissue elements is added (step 54);

computing a mass distribution of said patient based on the intermediate geometrical model and at least one of: said medical data 23 received, said at least one first image 21 and said at least one second image 22 (step 55);

computing biomechanical parameters based on said at least one among: said medical data, said at least one first image 21 and/or said at least one second image 22, said biomechanical parameters being related to biomechanical properties of said bone elements and said surrounding tissue elements (step 56); and generating said 3D biomechanical model 31 based on said intermediate geometrical model, said mass distribution and said biomechanical parameters (step 57).

As the 3D biomechanical model 31 may be complex and computationally intensive, it may not always be feasible for real-time applications or large-scale simulations. In such cases, a simplified model (e.g. surrogate model 139), may be computed to overcome these limitations.

The surrogate model 139 aims to capture the essential characteristics of the original 3D biomechanical model 31, while significantly reducing computational cost and complexity. This simplified representation allows for quicker computations, making it suitable for tasks such as real-time decision-making, optimization, or sensitivity analysis.

The device 1 for generating a 3D biomechanical model of a spine of a patient and assisting a user in planning a spine treatment for said patient's spine may therefore be associated with a device 2 for training an untuned machine learning surrogate model 39 so as to obtain a trained surrogate model 139 and a device 3 for computing, using the surrogate model 139 trained using the device 2, biomechanical performance indicators (that may be derived from the surrogate model 139 in the same manner as for the 3D biomechanical model 31) and post-treatment biomechanical performance indicator 235 comprising information concerning said patient's spine after performing at least one treatment act.

More precisely, a post-treatment biomechanical performance indicator 235 may encompass the calculation of biomechanical stresses between at least two bone elements after the treatment and/or the calculation of failure risks of a medical device newly implanted in the patient after the treatment. The post-treatment biomechanical performance indicators 235 may be derived from the surrogate model 139 in the same manner as the post-treatment biomechanical performance indicators 235 for the 3D biomechanical model 31.

Though the presently described devices 1, 2 and 3 are versatile and provided with several functions that can be carried out alternatively or in any cumulative way, other implementations within the scope of the present disclosure include devices having only parts of the present functionalities.

Each of the devices 1, 2 and 3 is advantageously an apparatus, or a physical part of an apparatus, designed, configured and/or adapted for performing the mentioned functions and produce the mentioned effects or results. In alternative implementations, any of the device 1, 2 and the device 3 is embodied as a set of apparatus or physical parts of apparatus, whether grouped in a same machine or in different, possibly remote, machines. The device 1 and/or 2 and/or the device 3 may e.g. have functions distributed over a cloud infrastructure and be available to users as a cloud-based service, or have remote functions accessible through an API.

The device 1, 2 and the device 3 may be integrated in a same apparatus or set of apparatus, and intended to same users. In other implementations, the structure of the device 1 may be completely independent of the structure of the device 2 and of the device 3, and may be provided for other users. For example, the device 3 may have a trained machine learning surrogate model 39 available to operators, wholly set from previous training effected upstream by other players with the device 2.

In what follows, the modules are to be understood as functional entities rather than material, physically distinct, components. They can consequently be embodied either as grouped together in a same tangible and concrete component, or distributed into several such components. Also, each of those modules is possibly itself shared between at least two physical components. In addition, the modules are implemented in hardware, software, firmware, or any mixed form thereof as well. They are preferably embodied within at least one processor of the device 2 or of the device 3.

Figure 6:
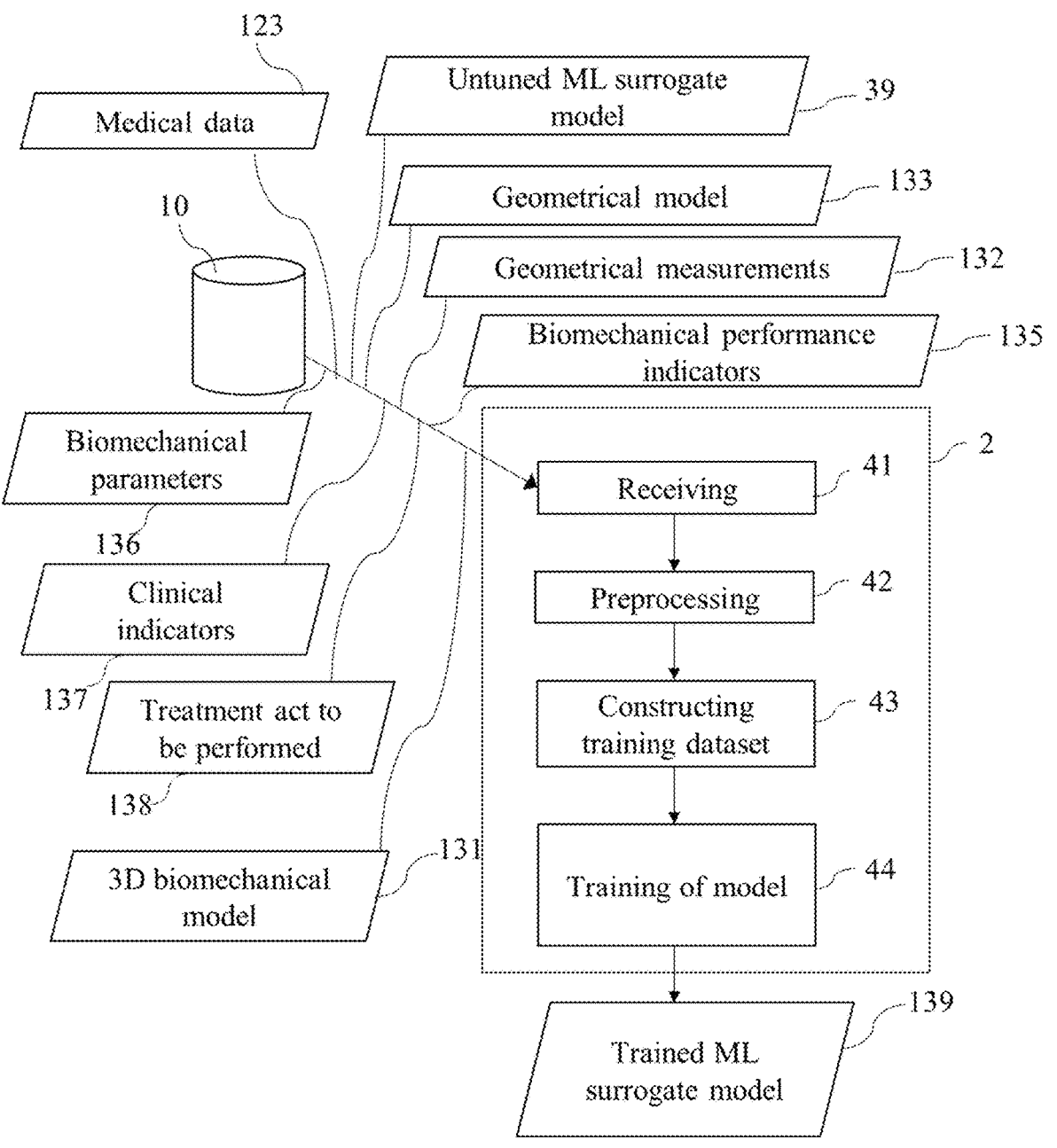
FIG. 6 is a block diagram representing schematically a particular mode of a device for training a machine learning surrogate model for computing at least one post-treatment biomechanical performance indicator of comprising information concerning said patient's spine after performing at least one treatment act compliant with the present disclosure.

As illustrated on FIG. 6, The device 2 comprises a module 41 for receiving for each subject of a plurality of subjects, the 3D biomechanical model 131 computed for said subject and the corresponding medical data 123 and biomechanical parameters 136, the geometrical model 133 computed for said subject, geometrical measurements 132 obtained using the geometrical model 133, biomechanical performance indicators 135 (pre-treatment), and clinical indicators 137 (pre-treatment) derived from the 3D biomechanical model 131. The module 41 may be further configured to receive the untuned machine learning surrogate model 39 and at least one treatment act 138 to be performed on the subject. These input data may be stored in one or more local or remote database(s) 10. The latter can take the form of storage resources available from any kind of appropriate storage means, which can be notably a RAM or an EEPROM (Electrically-Erasable Programmable Read-Only Memory) such as a Flash memory, possibly within an SSD (Solid-State Disk).

The device 2 further comprises optionally a module 42 for preprocessing the input data. For instance, series of Finite Elements Analysis and/or Multibody dynamics may be run to generate the training dataset needed to build the surrogate model.

The training set may be a hybrid dataset generated by solving a large series of detailed FEM models and augmented using clinical data.

The device may comprise a module 43 for the construction of the training dataset using the input data received by module 41.

The device 1 further comprises a module 44 configured to train the untuned machine learning surrogate model 39 using the training dataset constructed (or received) by module 43.

Once the training completed, module 44 is configured to output the trained machine learning surrogate model 139. The trained machine learning surrogate model 139 may then by stored in one or more local or remote database(s) 10. The latter can take the form of storage resources available from any kind of appropriate storage means, which can be notably a RAM or an EEPROM (Electrically-Erasable Programmable Read-Only Memory) such as a Flash memory, possibly within an SSD (Solid-State Disk).

In its automatic actions, the device 1 may for example execute the following process:

receiving for each subject of said plurality of subjects, the 3D biomechanical model 131 computed for said subject and the corresponding medical data 123 and biomechanical parameters 136, the geometrical model 33 computed for said subject, geometrical measurements 132 obtained using the geometrical model 133, biomechanical performance indicators 135 (pre-treatment), and clinical indicators 137 (pre-treatment) derived from the 3D biomechanical model 131 together with the untuned machine learning surrogate model, preprocessing the received data, constructing the training dataset, obtaining said trained machine learning surrogate model 139 by feeding said training dataset to the untuned machine learning surrogate model 39.

Figure 7:
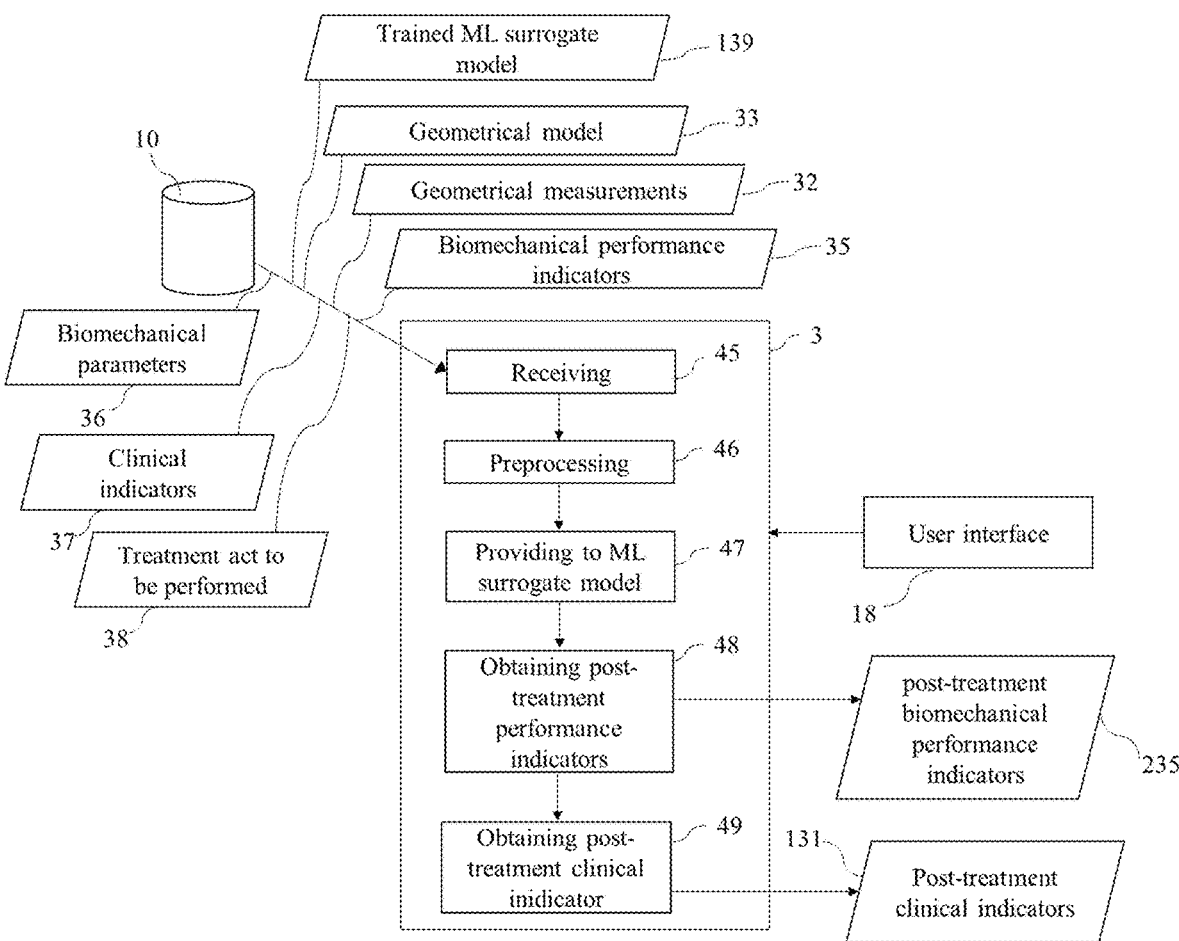
FIG. 7 is a block diagram representing schematically a particular mode of a device for computing at least one post-treatment biomechanical performance indicator comprising information concerning said patient's spine after performing at least one treatment act compliant with the present disclosure.

The present invention also relates to a device 3 for computing at least one post-treatment biomechanical performance indicator 235 comprising information concerning said patient's spine after performing at least one treatment act, using the trained machine learning surrogate model 139 obtained from the device 2, as described above. The device 3 will be described in reference to a particular function embodiment as illustrated in FIG. 7.

The device 3 is adapted to receive the geometrical model 33 obtained for the patient, the geometrical measurements 32 derived from said geometrical model 33, biomechanical performance indicators 35, biomechanical parameters 36, clinical indicators 37 and the treatment act 38 to be performed on said patient.

The device 3 is adapted to provide as an output post-treatment biomechanical performance indicator 235 comprising information concerning said patient's spine after performing at least one treatment act 131.

The device 3 comprises a module 45 for receiving the input data mentioned above, stored in one or more local or remote database(s) 10. The latter can take the form of storage resources available from any kind of appropriate storage means, which can be notably a RAM or an EEPROM (Electrically-Erasable Programmable Read-Only Memory) such as a Flash memory, possibly within an SSD (Solid-State Disk). In some embodiments, the trained machine learning surrogate model 139 is also received by module 15. The trained machine learning surrogate model 139 and all its parameters have been previously generated by a system including the device 2 for training. Alternatively, the trained machine learning surrogate model 139 and its parameters are received from a communication network.

The device 3 further comprises optionally a module 46 for preprocessing the input data.

The device 3 further comprises a module 47 configured to provide the input data to said trained machine learning surrogate model 139 so as to generate the corresponding post-treatment biomechanical performance indicators 235 (module 48).

Additionally, post-treatment clinical indicators 131 can be derived from the post-treatment biomechanical performance indicators 235 (for instance using module 49) to enhance diagnostic and treatment strategies. To that end, a machine learning model may be trained to generate the post-treatment clinical indicators 131 using a training dataset comprising for instance biomechanical performance indicators 35 paired with clinical indicators 37 obtained on a plurality of subjects and/or post-treatment biomechanical performance indicators 235 paired with post-treatment clinical indicators 131 obtained on a plurality of subjects and optionally with other data such as age, height, weight etc.

The device 1 and 3 may interact with a user interface 18, via which information can be entered and retrieved by a user. The user interface 18 includes any means appropriate for entering or retrieving data, information or instructions, notably visual, tactile and/or audio capacities that can encompass any or several of the following means as well known by a person skilled in the art: a screen, a keyboard, a trackball, a touchpad, a touchscreen, a loudspeaker, a voice recognition system.

In its automatic actions, the device 3 may for example execute the following process:

receiving the trained machine learning surrogate model 139 and the geometrical model 33 obtained for the patient, the corresponding geometrical measurements 32, biomechanical performance indicators 35, biomechanical parameters 36, clinical indicators 37 and the treatment act to be performed on said patient, optionally preprocessing the input data, providing said input data to said trained machine learning surrogate model 139 so as to obtain the corresponding post-treatment biomechanical performance indicators 235; and optionally obtaining clinical indicators 131 based on said post-treatment biomechanical performance indicators 235.

Further to the generation of the surrogate model 139, the device 2 may be configured to compute at least one treatment plan. This plan is constructed by implementing a predefined set of rules which constraints the geometrical parameters, clinical indicators and biomechanical performance indicators derived from the surrogate model 139. The rules and the choice of treatment plan may be set based on probabilistic medical indicators calculated on the reduced biomechanical model.

A particular apparatus may embody the device 1 as well as the device 2 and/or 3 described above. It corresponds for example to a workstation, a laptop, a tablet, a smartphone, or a head-mounted display (HMD).

That apparatus comprises the following elements, connected to each other by a bus of addresses and data that also transports a clock signal:

a microprocessor (or CPU);

a graphics card comprising several Graphical Processing Units (or GPUs) and a Graphical Random Access Memory (GRAM); the GPUs are quite suited to image processing, due to their highly parallel structure;

a non-volatile memory of ROM type;

a RAM;

one or several I/O (Input/Output) devices such as for example a keyboard, a mouse, a trackball, a webcam; other modes for introduction of commands such as for example vocal recognition are also possible;

a power source; and a radiofrequency unit.

According to a variant, the power supply is external to the apparatus.

The apparatus also comprises a display device of display screen type directly connected to the graphics card to display synthesized images calculated and composed in the graphics card. According to a variant, a display device is external to the apparatus and is connected thereto by a cable or wirelessly for transmitting the display signals. The apparatus, for example through the graphics card, comprises an interface for transmission or connection adapted to transmit a display signal to an external display means such as for example an LCD or plasma screen or a video-projector. In this respect, the RF unit can be used for wireless transmissions.

It is noted that the word "register" used hereinafter in the description of memories can designate in each of the memories mentioned, a memory zone of low capacity (some binary data) as well as a memory zone of large capacity (enabling a whole program to be stored or all or part of the data representative of data calculated or to be displayed). Also, the registers represented for the RAM and the GRAM can be arranged and constituted in any manner, and each of them does not necessarily correspond to adjacent memory locations and can be distributed otherwise (which covers notably the situation in which one register includes several smaller registers).

When switched-on, the microprocessor loads and executes the instructions of the program contained in the RAM.

As will be understood by a skilled person, the presence of the graphics card is not mandatory, and can be replaced with entire CPU processing and/or simpler visualization implementations.

The invention claimed is:

1. A computer implemented method for generating a 3D biomechanical model of a spine of a patient and assisting a user in planning a spine treatment for said patient's spine, said 3D biomechanical model being representative of bone elements associated to said patient's spine, surrounding tissue elements and associated biomechanical parameters, said method comprising:

receiving medical data related to said patient, said medical data comprising at least: a weight, a height, clinical information and morphological information;

receiving at least one first image of said patient, said at least one first image being previously acquired from said patient in a first position, and comprising at least one first representation of bone elements in said first position;

receiving at least one second image of said patient, said at least one second image being previously acquired from said patient in a second position different from said first position, and comprising at least one second representation of said bone elements in said second position;

generating a geometrical model of said patient's spine based on said at least one first image and said at least one second image, said geometrical model being representative of said bone elements of said patient's spine;

generating an intermediate geometrical model based on said geometrical model on which a model of the surrounding tissue elements is added;

computing a mass distribution of said patient based on the intermediate geometrical model and at least one of: said medical data received, said at least one first image and said at least one second image;

computing biomechanical parameters based on said at least one among: said medical data, said at least one first image and/or said at least one second image, said biomechanical parameters being related to biomechanical properties of said bone elements and said surrounding tissue elements;

generating said 3D biomechanical model representative of bone elements associated to said patient's spine, surrounding tissue elements and associated biomechanical parameters based on said intermediate geometrical model, said mass distribution and said biomechanical parameters; and outputting said geometrical model and said 3D biomechanical model to assist said user in scheduling said surgery on said patient's spine wherein said method further comprises:

applying at least one load to said 3D biomechanical model, said load including at least one of gravity load, flexion load and extension load;

computing biomechanical performance indicators related to biomechanical stress between at least two bone elements based on the 3D biomechanical model obtained after said load has been applied; and computing clinical indicators based on said biomechanical performance indicators.

2. The method according to claim 1, wherein said method further comprises computing geometrical measurements on said geometrical model, said geometrical measurements being related to geometrical parameters computed between at least two bone elements of the geometrical model.

3. The method according to claim 2, further comprising computing, using a surrogate model, at least one post-treatment biomechanical performance indicator comprising information concerning said patient's spine after performing at least one treatment act, said surrogate model being a machine learning model, previously trained on a training dataset, said surrogate model being configured to receive as input said geometrical model, said geometrical measurements, said biomechanical parameters, said biomechanical performance indicators, said clinical indicators, and said at least one treatment act to be performed, wherein said training dataset comprises a plurality of training sample obtained from a plurality of subjects, each training sample comprising a 3D biomechanical model of a spine of a subject and the corresponding medical data, geometrical model, geometrical measurements, biomechanical parameters, biomechanical performance indicators, clinical indicators, and treatment acts.

4. The method according to claim 3, further comprising computing at least one treatment plan by using a set of rules applied to said geometrical parameters and to said biomechanical performance indicators, said clinical indicators and said at least one post-treatment biomechanical performance indicator, said at least one treatment plan comprising at least one treatment act to perform on said patient's spine.

5. The method according to claim 4, wherein said at least one post-treatment biomechanical performance indicator is associated to information comprising computing probabilistic medical indicators representing a probability of mechanical failure of at least one of an implanted device, vertebral bones and intervertebral disks.

6. The method according to claim 4, wherein computing at least one treatment plan comprises comparing said at least one post-treatment biomechanical performance indicator, and the associated information, across different treatment plans to classify the treatment plans as function of a probability of mechanical failure.

7. The method according to claim 1, wherein said at least one first image comprises at least one 3D image and said at least one second image comprises at least one 2D image.

8. The method according to claim 1, wherein generating said geometrical model of said patient's spine comprises:

selecting at least one bone element of interest among the bone elements associated to said patient's spine;

receiving at least one 3D segmentation mask of at least one bone element represented in the first 3D image including the bone element of interest, at least one associated label and at least one landmark calculated for said at least one bone element represented in said at least one first 3D image, and receiving at least one label associated to at least one bone element represented in said at least one second 2D image and at least one landmark calculated for said at least one bone element represented in said at least one second 2D image;

for each bone element of interest:

obtaining from said first segmentation mask at least one 3D reduced first image comprising said bone element of interest and a surrounding region of said bone element of interest;

obtaining at least one 2D reduced second image comprising said bone element of interest and a surrounding region of said bone element of interest;

performing an initial alignment between said at least one 3D reduced first image and said at least one 2D reduced second image;

generating at least one 2D projection of said at least one 3D reduced first image; and registering said at least one 2D projection to said at least one 2D reduced second image with respect to said bone element of interest so as to obtain optimized transformation parameters corresponding to said bone element of interest; and reconstructing said geometrical model using the at least one 3D segmentation mask and the optimized transformation parameters obtained for each corresponding bone element of interest, so that the geometrical model provides a representation of at least one portion of the patient's spine in the second position.

9. The method according to claim 8, wherein said at least one landmark for the at least one first 3D image and second 2D image is chosen from the following: a center, and/or corner points of said at least one bone element.

10. The method according to claim 8, wherein reconstructing said geometrical model comprises:

for each bone element of interest, applying the corresponding optimized transformation parameters to the bone element of interest in the at least one 3D segmentation mask, obtaining an individual segmentation mask corresponding to said bone element of interest in the second position; and verifying and removing interpenetrations in between individual segmentation masks.

11. The method according to claim 1, wherein said 3D biomechanical model is a finite-element model.

12. The method according to claim 1, wherein said plurality of bone element comprises at least one vertebra among S1 to C1 and/or at least one intervertebral disc, and/or at least one surrounding element, said surrounding element comprising at least one of: a hip, a femur head, a rib, ligaments and muscles.

13. A non-transitory computer-readable medium comprising instructions which, when executed by a computer, cause the computer to carry out the method according to claim 1.

* * * * *